(12) United States Patent
Anker

(10) Patent No.: US 8,483,824 B2
(45) Date of Patent: Jul. 9, 2013

(54) METHOD FOR ENHANCING THE PERFORMANCE AND GENERAL CONDITION OF A SUBJECT

(75) Inventor: Stefan Anker, Berlin (DE)

(73) Assignee: Stefan Anker, Berlin (DE)

( * ) Notice: Subject to any disclaimer, the term of this patent is extended or adjusted under 35 U.S.C. 154(b) by 846 days.

(21) Appl. No.: 12/088,466

(22) PCT Filed: Sep. 28, 2006

(86) PCT No.: PCT/EP2006/009530
§ 371 (c)(1),
(2), (4) Date: Jun. 16, 2008

(87) PCT Pub. No.: WO2007/039263
PCT Pub. Date: Apr. 12, 2007

(65) Prior Publication Data
US 2009/0248101 A1    Oct. 1, 2009

(30) Foreign Application Priority Data

Sep. 28, 2005 (DE) .......................... 10 2005 046 539

(51) Int. Cl.
*A61N 1/00*    (2006.01)
*A61B 5/04*    (2006.01)

(52) U.S. Cl.
USPC ......... 607/9; 607/4; 607/6; 607/119; 600/584

(58) Field of Classification Search
USPC ............... 607/4, 6, 9, 119; 600/584
See application file for complete search history.

(56) References Cited

U.S. PATENT DOCUMENTS

| | | | |
|---|---|---|---|
| 3,391,697 A | 7/1968 | Greatbatch | |
| 6,901,296 B1* | 5/2005 | Whitehurst et al. | 607/50 |
| 2004/0098075 A1* | 5/2004 | Lee | 607/122 |
| 2004/0186531 A1* | 9/2004 | Jahns et al. | 607/48 |
| 2004/0215252 A1 | 10/2004 | Verbeek et al. | |
| 2004/0230229 A1 | 11/2004 | Lovett et al. | |
| 2005/0065567 A1* | 3/2005 | Lee et al. | 607/17 |
| 2006/0100668 A1* | 5/2006 | Ben-David et al. | 607/2 |

OTHER PUBLICATIONS

Morgenthaler, NG, et al., "Sensitive Immunoluminometric Assay for the Detection of Procalcitonin," Clin Chem 2002; 48: 788-790.
Morgenthaler, NG, et al., "Immunoluminometric Assay for the Midregion of Pro-Atrial Natriuretic Peptide in Human Plasma," Clin Chem 2004; 50: 234-236.
Christ-Crain, M., et al., "Effect of Procalcitonin-guided Treatment on Antibiotic Use and Outcome in Lower Respiratory Tract Infections: Cluster-randomised, Single-blinded Intervention Trial," Lancet 2004; 363: 600-607.

* cited by examiner

*Primary Examiner* — Nicole F Lavert
(74) *Attorney, Agent, or Firm* — Pharmaceutical Patent Attorneys, LLC

(57) ABSTRACT

A method of treating patients in need of heart beat regulation or for preventing the development of cardiac arrhythmias, wherein the patients are not suffering from cardiac illness, by regulating heart beat using a cardiac pacemaker and reducing patient risk of developing a ventricular arrhythmia, wherein the risk is associated with an underlying patient illness, and wherein the patient does not suffer from cardiac illness, by regulating the patient's heart beat using a cardiac pacemaker.

30 Claims, 14 Drawing Sheets

This graph shows that patients with pancreatic cancer who have a VT on 24 hour ECG have significantly raised plasma levels of the natriuretic peptide MR-proANP.

ANOVA p-value: p=0.0125

Mean levels of MR-pro ANP in pmol/L

Means Table for MR-proANP

| | Count | Mean | Std. Dev. | Std. Err. |
|---|---|---|---|---|
| ohne | 34 | 88,071 | 55,410 | 9,503 |
| VES | 2 | 50,450 | 23,971 | 16,950 |
| VT | 3 | 210,833 | 179,476 | 103,620 |

Fisher's PLSD for MR-proANP in pmol/L
Effect: VT / VES / ohne
Significance Level: 5 %

| | Mean Diff. | Crit. Diff | P-Value | |
|---|---|---|---|---|
| ohne, VES | 37,621 | 100,300 | ,4518 | |
| ohne, VT | -122,763 | 83,024 | ,0049 | S |
| VES, VT | -160,383 | 125,838 | ,0139 | S |

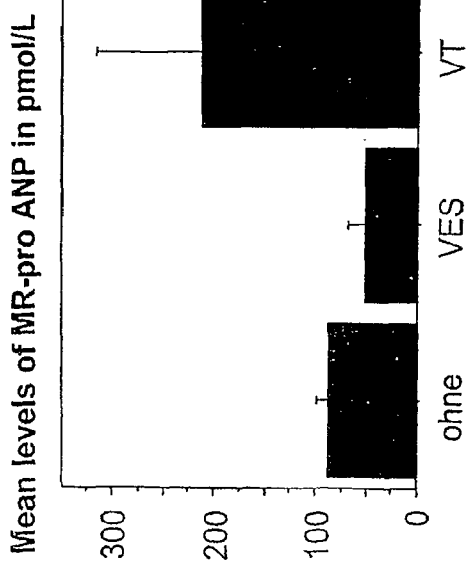

Figure 1
This graph shows that patients with pancreatic cancer who have a VT on 24 hour ECG have significantly raised plasma levels of the natriuretic peptide MR-proANP.

ANOVA p-value: p=0.0125

Means Table for MR-proANP

| | Count | Mean | Std. Dev. | Std. Err. |
|---|---|---|---|---|
| ohne | 34 | 88,071 | 55,410 | 9,503 |
| VES | 2 | 50,450 | 23,971 | 16,950 |
| VT | 3 | 210,833 | 179,476 | 103,620 |

Fisher's PLSD for MR-proANP in pmol/L
Effect: VT / VES / ohne
Significance Level: 5 %

| | Mean Diff. | Crit. Diff | P-Value | |
|---|---|---|---|---|
| ohne, VES | 37,621 | 100,300 | ,4518 | |
| ohne, VT | -122,763 | 83,024 | ,0049 | S |
| VES, VT | -160,383 | 125,838 | ,0139 | S |

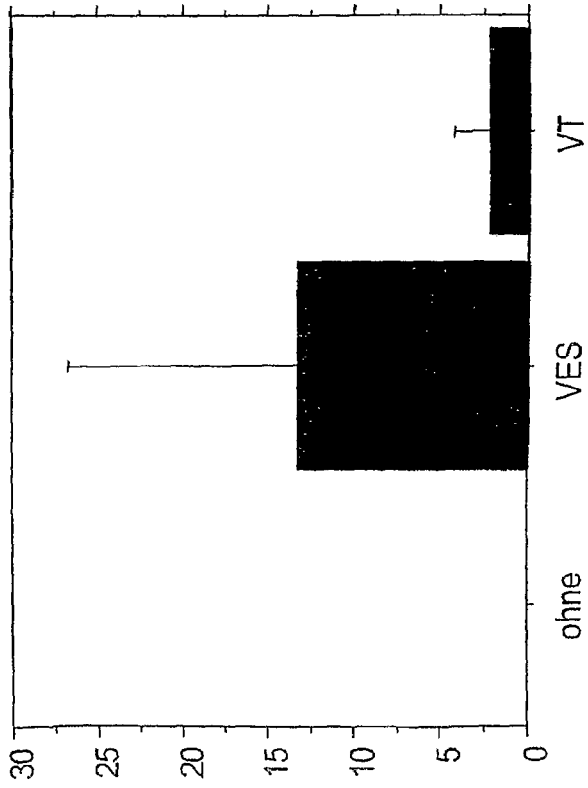

Figure 2
This graph shows that patients with pancreatic cancer who have a VT (mean 2.16 ng/mL) or have >10000 VES (mean 13.358 ng/mL) on 24 hour ECG have significantly raised plasma levels of the biomarker procalcitonin compared to patients without such arrythmias (mean 0.048 ng/mL).

ANOVA p-value: p<0.0001

Means Table for Procalcitonin in ng/mL

|  | Count | Mean | Std. Dev. | Std. Err. |
|---|---|---|---|---|
| ohne | 34 | ,048 | ,044 | ,008 |
| VES | 2 | 13,358 | 18,869 | 13,342 |
| VT | 3 | 2,160 | 3,689 | 2,130 |

Fisher's PLSD for Procalcitonin in ng/mL
Effect: VT / VES / ohne
Significance Level: 5 %

|  | Mean Diff. | Crit. Diff | P-Value |  |
|---|---|---|---|---|
| ohne, VES | -13,310 | 4,815 | <,0001 | S |
| ohne, VT | -2,113 | 3,986 | ,2896 |  |
| VES, VT | 11,197 | 6,041 | ,0006 | S |

Figure 3

Table set 1
This page indicates the general study group characteristics age [A], body weight [B], body mass index [C], and heart rate [D].

A

Unpaired t-test for age in years
Grouping Variable: VT/VES>10k y/n

| | Mean Diff. | DF | t-Value | P-Value |
|---|---|---|---|---|
| n, y | 1,177 | 42 | ,290 | ,7731 |

| | Count | Mean | Variance | Std. Dev. | Std. Err |
|---|---|---|---|---|---|
| n | 38 | 58,669 | 79,776 | 8,932 | 1,449 |
| y | 6 | 57,492 | 125,113 | 11,185 | 4,566 |

B

Unpaired t-test for body weight in kg
Grouping Variable: VT/VES>10k y/n

| | Mean Diff. | DF | t-Value | P-Value |
|---|---|---|---|---|
| n, y | -6,252 | 42 | -1,296 | ,2021 |

| | Count | Mean | Variance | Std. Dev. | Std. Err |
|---|---|---|---|---|---|
| n | 38 | 66,882 | 118,843 | 10,901 | 1,768 |
| y | 6 | 73,133 | 133,851 | 11,569 | 4,723 |

C

Unpaired t-test for body mass index in kg/m2
Grouping Variable: VT/VES>10k y/n

| | Mean Diff. | DF | t-Value | P-Value |
|---|---|---|---|---|
| n, y | -,121 | 42 | -,086 | ,9316 |

| | Count | Mean | Variance | Std. Dev. | Std. Err |
|---|---|---|---|---|---|
| n | 38 | 23,092 | 10,207 | 3,195 | ,518 |
| y | 6 | 23,212 | 9,304 | 3,050 | 1,245 |

D

Unpaired t-test for heart rate in 1/min
Grouping Variable: VT/VES>10k y/n

| | Mean Diff. | DF | t-Value | P-Value |
|---|---|---|---|---|
| n, y | 2,967 | 39 | ,665 | ,5098 |

| | Count | Mean | Variance | Std. Dev. | Std. Err |
|---|---|---|---|---|---|
| n | 35 | 72,800 | 82,106 | 9,061 | 1,532 |
| y | 6 | 69,833 | 236,167 | 15,368 | 6,274 |

Figure 4

Table set 2
This page indicates the study group characteristics NYHA class [E], UICC cancer disease severity [F] and Karnofsky index [G].

E

Unpaired t-test for NYHA class
Grouping Variable: VT/VES>10k y/n

| | Mean Diff. | DF | t-Value | P-Value |
|---|---|---|---|---|
| n, y | ,007 | 39 | ,017 | ,9863 |

| | Count | Mean | Variance | Std. Dev. | Std. Err |
|---|---|---|---|---|---|
| n | 37 | 1,757 | ,578 | ,760 | ,125 |
| y | 4 | 1,750 | ,250 | ,500 | ,250 |

F

Unpaired t-test for UICC cancer disease severity
Grouping Variable: VT/VES>10k y/n

| | Mean Diff. | DF | t-Value | P-Value |
|---|---|---|---|---|
| n, y | -,139 | 40 | -,225 | ,8230 |

| | Count | Mean | Variance | Std. Dev. | Std. Err |
|---|---|---|---|---|---|
| n | 36 | 2,861 | 1,894 | 1,376 | ,229 |
| y | 6 | 3,000 | 2,400 | 1,549 | ,632 |

G

Unpaired t-test for Karnofsky-Index in %
Grouping Variable: VT/VES>10k y/n

| | Mean Diff. | DF | t-Value | P-Value |
|---|---|---|---|---|
| n, y | -5,784 | 40 | -1,520 | ,1363 |

| | Count | Mean | Variance | Std. Dev. | Std. Err |
|---|---|---|---|---|---|
| n | 37 | 86,216 | 68,619 | 8,284 | 1,362 |
| y | 5 | 92,000 | 20,000 | 4,472 | 2,000 |

Figure 5

Table set 3A
This page indicates the study group characteristics cardiac left ventricular ejection fraction (LVEF triplan [H]), cardiac size (LVEDD [I]), and systolic blood pressure [K].

H

Unpaired t-test for LVEF triplan in %
Grouping Variable: VT/VES>10k y/n

| n, y | Mean Diff. | DF | t-Value | P-Value |
|---|---|---|---|---|
| | -1,648 | 22 | -,338 | ,7389 |

| | Count | Mean | Variance | Std. Dev. | Std. Err |
|---|---|---|---|---|---|
| n | 20 | 58,602 | 72,583 | 8,520 | 1,905 |
| y | 4 | 60,250 | 122,917 | 11,087 | 5,543 |

I

Unpaired t-test for LVEDD in mm
Grouping Variable: VT/VES>10k y/n

| n, y | Mean Diff. | DF | t-Value | P-Value |
|---|---|---|---|---|
| | -4,233 | 29 | -1,102 | ,2797 |

| | Count | Mean | Variance | Std. Dev. | Std. Err |
|---|---|---|---|---|---|
| n | 26 | 47,027 | 57,305 | 7,570 | 1,485 |
| y | 5 | 51,260 | 90,728 | 9,525 | 4,260 |

K

Unpaired t-test for systolic blood pressure in mmHg
Grouping Variable: VT/VES>10k y/n

| n, y | Mean Diff. | DF | t-Value | P-Value |
|---|---|---|---|---|
| | -8,095 | 39 | -,983 | ,3315 |

| | Count | Mean | Variance | Std. Dev. | Std. Err |
|---|---|---|---|---|---|
| n | 35 | 127,571 | 358,017 | 18,921 | 3,198 |
| y | 6 | 135,667 | 273,467 | 16,537 | 6,751 |

Figure 6

Table set 3B

This page indicates the study group characteristics exercise time [L], objective exercise capacity (peak VO2 per kg body weight in mL/kg/min [M]), and total exercise capacity (i.e. total peak VO2 in mL/min [N]).

L Unpaired t-test for exercise time in seconds
Grouping Variable: VT/VES>10k y/n

|  | Mean Diff. | DF | t-Value | P-Value |
|---|---|---|---|---|
| n, y | 72,100 | 39 | ,519 | ,6065 |

|  | Count | Mean | Variance | Std. Dev. | Std. Err |
|---|---|---|---|---|---|
| n | 35 | 784,600 | 90450,071 | 300,749 | 50,836 |
| y | 6 | 712,500 | 155331,100 | 394,121 | 160,899 |

M Unpaired t-test for Peak VO2 in mL/min/kg
Grouping Variable: VT/VES>10k y/n

|  | Mean Diff. | DF | t-Value | P-Value |
|---|---|---|---|---|
| n, y | 4,718 | 39 | 1,775 | ,0837 |

|  | Count | Mean | Variance | Std. Dev. | Std. Err |
|---|---|---|---|---|---|
| n | 35 | 21,134 | 35,922 | 5,993 | 1,013 |
| y | 6 | 16,417 | 38,030 | 6,167 | 2,518 |

N Unpaired t-test for total exercise capacity, i.e. total peak VO2 in mL/min
Grouping Variable: VT/VES>10k y/n

|  | Mean Diff. | DF | t-Value | P-Value |
|---|---|---|---|---|
| n, y | 193,368 | 39 | ,986 | ,3301 |

|  | Count | Mean | Variance | Std. Dev. | Std. Err |
|---|---|---|---|---|---|
| n | 35 | 1441,793 | 183072,751 | 427,870 | 72,323 |
| y | 6 | 1248,425 | 291018,795 | 539,462 | 220,234 |

Table set 4
This page indicates the study group characteristics MR-proANP [O] level and procalcitonin level [P].

Figure 8

Kaplan-Meier-Survival Analysis

Survival table for patients with pancreatic cancer and <u>without</u> significant arrythmia (VT or VES >10000 in 24 hour ECG): at 12 months 44.1% of patients have died.

Survival Summary Table for Follow-up in days
Censor Variable: Survival
Grouping Variable: VT/VES>10k y/n

|       | # Obs. | # Events | # Censored | % Censored |
|-------|--------|----------|------------|------------|
| n     | 38     | 12       | 26         | 68,421     |
| y     | 6      | 4        | 2          | 33,333     |
| Total | 44     | 16       | 28         | 63,636     |

Figure 9  Kaplan-Meier Survival Table for Follow-up in days
Censor Variable: Survival, Group: patients *without* significant arrythmias

| Time | Status | Cum. Surv. | Cum. Fail. | Surv. Std. Err. |
|---|---|---|---|---|
| 0.000 | | 1.000 | 0.000 | 0.000 |
| 46.000 | Censored | 1.000 | 0.000 | 0.000 |
| 46.000 | Censored | 1.000 | 0.000 | 0.000 |
| 47.000 | Uncensored | .972 | .028 | .027 |
| 47.000 | Censored | .972 | .028 | .027 |
| 53.000 | Censored | .972 | .028 | .027 |
| 55.000 | Censored | .972 | .028 | .027 |
| 55.000 | Censored | .972 | .028 | .027 |
| 57.000 | Uncensored | .941 | .059 | .041 |
| 66.000 | Uncensored | .909 | .091 | .050 |
| 74.000 | Censored | .909 | .091 | .050 |
| 75.000 | Censored | .909 | .091 | .050 |
| 78.000 | Uncensored | .876 | .124 | .058 |
| 91.000 | Censored | .876 | .124 | .058 |
| 103.000 | Censored | .876 | .124 | .058 |
| 104.000 | Censored | .876 | .124 | .058 |
| 131.000 | Censored | .876 | .124 | .058 |
| 161.000 | Uncensored | .836 | .164 | .068 |
| 165.000 | Uncensored | .796 | .204 | .075 |
| 166.000 | Censored | .796 | .204 | .075 |
| 172.000 | Censored | .796 | .204 | .075 |
| 174.000 | Censored | .796 | .204 | .075 |
| 200.000 | Censored | .796 | .204 | .075 |
| 201.000 | Censored | .796 | .204 | .075 |
| 214.000 | Uncensored | .743 | .257 | .087 |
| 228.000 | Censored | .743 | .257 | .087 |
| 248.000 | Uncensored | .686 | .314 | .097 |
| 259.000 | Uncensored | .629 | .371 | .105 |
| 342.000 | Censored | .629 | .371 | .105 |
| 362.000 | Censored | .629 | .371 | .105 |
| 363.000 | Uncensored | .559 | .441 | .114 |
| 371.000 | Censored | .559 | .441 | .114 |
| 383.000 | Uncensored | .479 | .521 | .123 |
| 440.000 | Uncensored | .399 | .601 | .125 |
| 482.000 | Censored | .399 | .601 | .125 |
| 509.000 | Censored | .399 | .601 | .125 |
| 557.000 | Censored | .399 | .601 | .125 |
| 565.000 | Censored | .399 | .601 | .125 |
| 608.000 | Censored | .399 | .601 | .125 |

Figure 10A

Kaplan-Meier-Survival Analysis
Survival table for patients with pancreatic cancer and
VT or VES >10000 in 24 hour ECG:
at 12 months 68.8% of patients have died.

Kaplan-Meier Survival Table for Follow-up in days
Censor Variable: Survival, Group: patients with significant arythmias,
i.e. VT or >10000 VES in 24 hour ECG

| Time | Status | Cum. Surv. | Cum. Fail. | Surv. Std. Err. |
|---|---|---|---|---|
| 0,000 | | 1,000 | 0,000 | 0,000 |
| 57,000 | Uncensored | 0,833 | 0,167 | 0,152 |
| 173,000 | Censored | 0,833 | 0,167 | 0,152 |
| 175,000 | Uncensored | 0,625 | 0,375 | 0,213 |
| 201,000 | Censored | 0,625 | 0,375 | 0,213 |
| 326,000 | Uncensored | 0,313 | 0,688 | 0,245 |
| 384,000 | Uncensored | 0,000 | 1,000 | 0,000 |

Figure 10B

Kaplan-Meier-Survival Analysis Survival Graph
Patients with pancreatic cancer and significant
arrythmia (arrow) have poorer survival.
Kaplan-Meier Survival Plot for Follow-up in days
Censor Variable: Survival,
Group: patients with vs without significant arrythmias,
i.e. VT or >10000 VES in 24 hour ECG

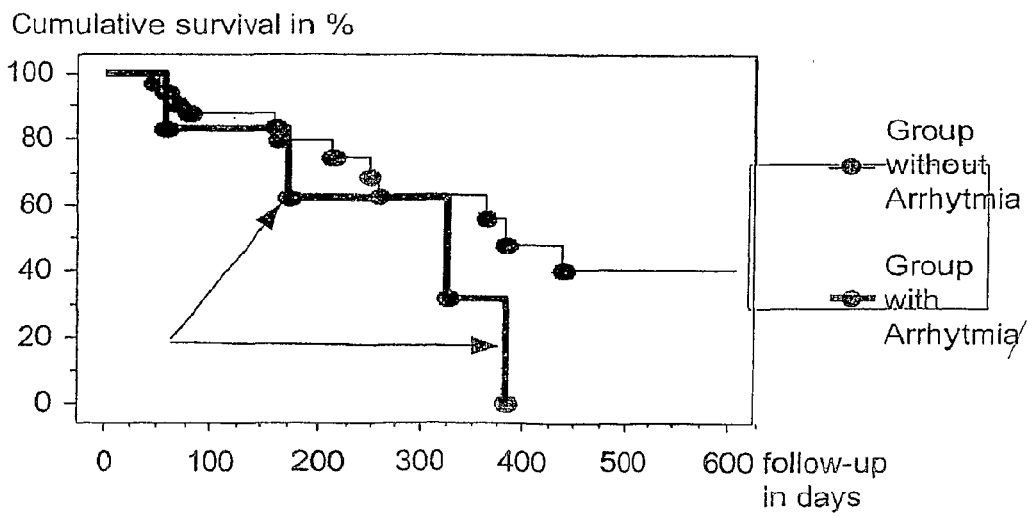

Figure 11A

Cox-Proportional Hazard Analysis
Main result: per 1000 VES detected
in a 24 hour ECG of a patient with
Pancreatic cancer, the risk of death
increases by 5.3%.
44 patients
16 events
%censored: 63.6
P-value: 0.1231

Confidence Intervals for Follow-up in days
Censor Variable: survival
Model: Proportional Hazards

|  | follow-up in days Exp(Coef) | 95% Lower | 95% Upper |
|---|---|---|---|
| VES total/1000 | 1,053 | ,986 | 1,125 |

Baseline Cum. Survival Plot for Follow-up in days
Censor Variable surival
Model: Proportional Hazards

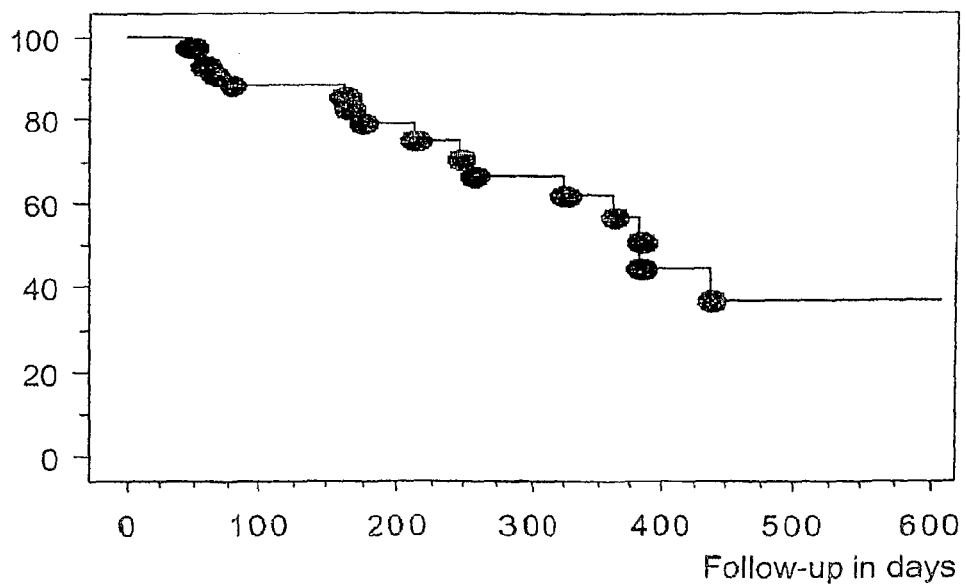

Figure 11B

Cox-Proportional Hazard Analysis
Main result: per 1 ng/mL higher
plasma level of procalcitonin
in a patient with pancreatic cancer,
the risk of death increases by 13.2%.
($p<0.05$)
46 patients
18 events
%censored: 60.9
P-value: 0.0056

Model Coefficients for Follow-up in days

Censor Variable: survival

Model: Proportional Hazards

|  | Exp(Coef) | 95% Lower | 95% Upper |
|---|---|---|---|
| Procalcitonin in ng/mL | 1,132 | 1,037 | 1,235 |

Baseline Cum. Survival Plot for Follow-up in days
Censor Variable surival
Model: Proportional Hazards
Cumulative survival in %

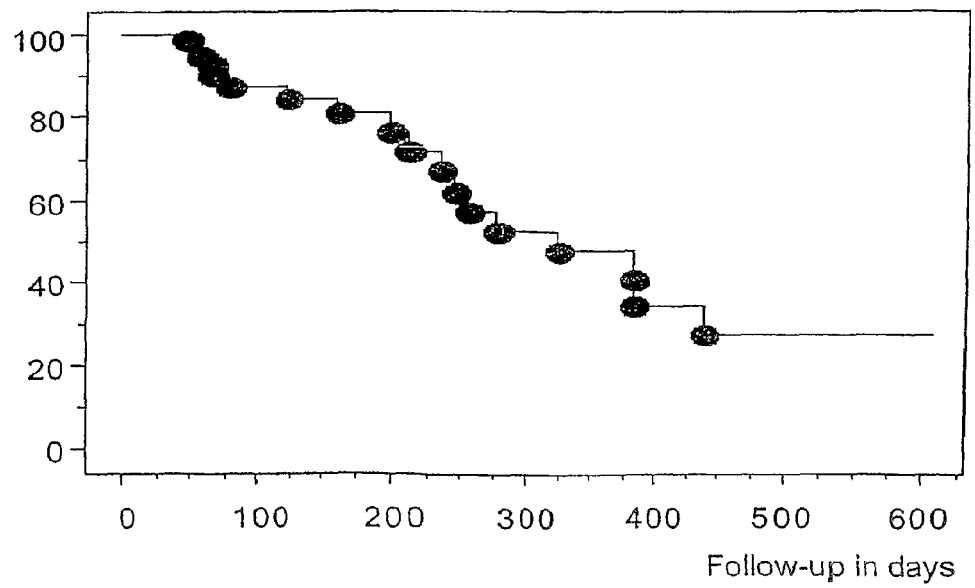

Figure 12

Regression analysis of MR-proANP level vs exercise capacity of patients, i.e. peak VO2.
Main results:
1. In 43 patients, there is a significant and inverse relationship between objective symptom status, i.e. peak VO2, and the level of natriuretic peptide MR-proANP: r= -0.317, p=0.038.
2. Considering the upper limited of normal for MR-proANP in healthy people (49 pmol/L, indicated by the dashed line), the graph indicates that 40 of 43 patients, i.e. 93% of cancer patients, have raised levels of natriuretic peptides.

Regression Summary
Peak VO2 in mL/min/kg at baseline vs MR-proANP level in pmol/L

| | |
|---|---|
| Count | 43 |
| Num. Missing | 10 |
| R | ,317 |
| R Squared | ,101 |
| Adjusted R Squared | ,079 |
| RMS Residual | 5,808 |

Regression Plot

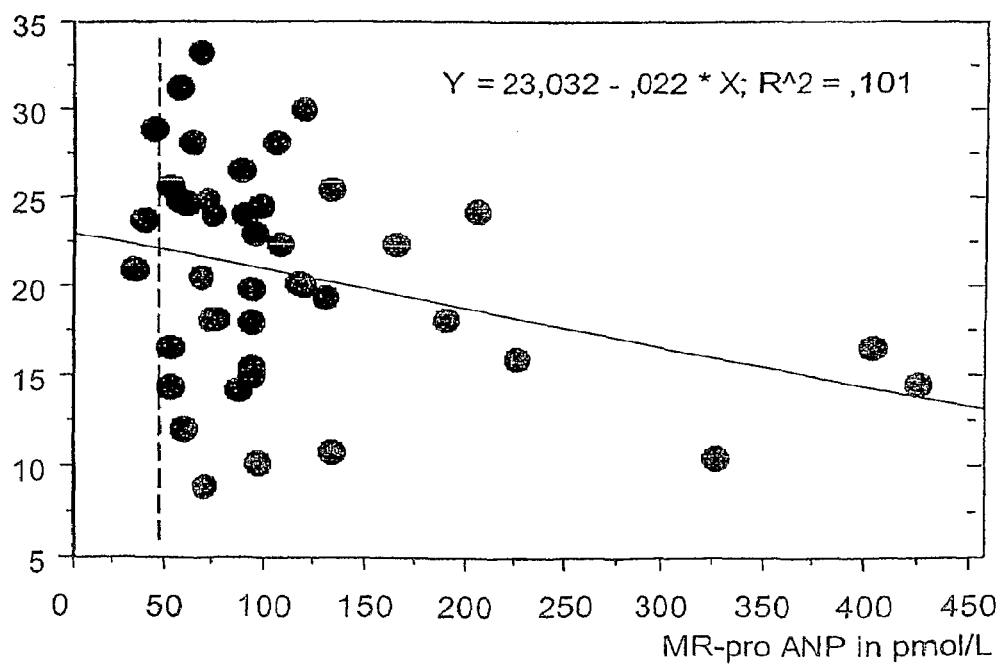

Figure 13

Regression analysis of procalcitonin, i.e. PCT, level vs the frequency of VES in the 24 hour ECG at baseline
Main result:
In 39 patients, there is a significant positive relationship between the biomarker PCT and the arrythmia frequency:
r= 0.62, p<0.0001

Regression Summary

VES in 24 hours ECG at baseline vs procalcitonin in ng/mL

| Count | 39 |
|---|---|
| Num. Missing | 14 |
| R | .617 |
| R Squared | .380 |
| Adjusted R Squared | .363 |
| RMS Residual | 3229,041 |

Regression Plot

VES count in 24 hour ECG at baseline

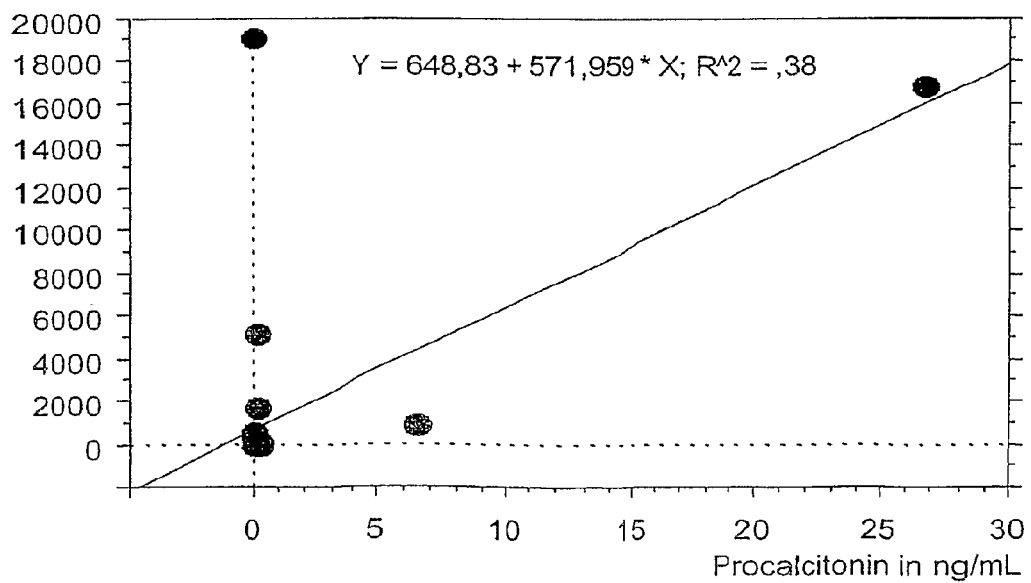

$Y = 648,83 + 571,959 * X; R^2 = ,38$

Procalcitonin in ng/mL

METHOD FOR ENHANCING THE PERFORMANCE AND GENERAL CONDITION OF A SUBJECT

CROSS REFERENCE TO RELATED APPLICATION

This application is a 35 U.S.C. 371 National Phase Entry Application from PCT/EP2006/009530, filed Sep. 28, 2006, which claims the benefit of German Patent Application No. 10 2005 046 539.0 filed on Sep. 28, 2006, and published as DE102005046539(A1), the disclosure of which is incorporated herein by reference.

The invention concerns the therapy with a cardiac resynchronisation device (CRT) and/or therapy with an automated internal cardiac defibrillator (ICD) for treating patients with any cancer or patients with cachexia due to acute or chronic illness other than cardiac illness, including malignant tumor disease, COPD, chronic renal failure, liver cirrhosis, chronic infections, and/or AIDS. Areas of application are the life sciences, in particular medicine and medical technology.

BACKGROUND OF THE INVENTION

1. Field of the Invention

It is common medical knowledge that death rates in patients with cachexia are higher than death rates in patients without cachexia in any chronic illness.

2. Description of the Related Art

The aim of the present invention is therefore to make available an easy and efficient method for the treatment of patients, in particular human patients, suffering from cancer or cachexia due to an acute or chronic illness other than cardiac illness. To this end, the implementation of the actions as described in the claims provides appropriate means to fulfill these demands in a satisfying manner.

BRIEF SUMMARY OF THE INVENTION

Accordingly, the technical features of the invention in its different embodiments as specified in the claims, in the specification or in the examples are also implemented as a method for the preparation of a patient, in particular a human patient, having cancer or cachexia due to an acute or chronic illness other than cardiac illness, for/to a treatment for reducing and/or reversing weight loss and/or reversing muscle wasting by using a cardiac pace maker for regulating the heart beat of the patient.

BRIEF DESCRIPTION OF THE SEVERAL VIEWS OF THE INVENTION

FIG. 1 shows a graph of the mean levels of MR-pro ANP in pmol/L of pancreatic cancer patients and Tables providing statistical analysis of the graphed levels.

FIG. 2 shows a graph of the mean levels of Procalcitonin in ng/mL of pancreatic cancer patients and Tables providing statistical analysis of the graphed levels.

Figure 7:
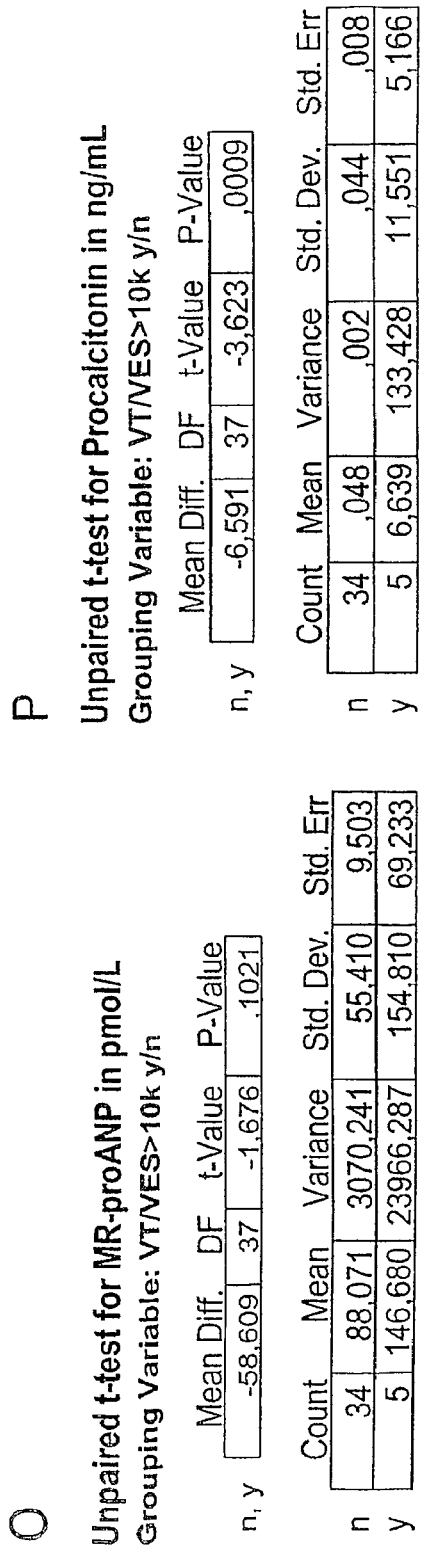

FIG. 3 indicates the general study group characteristics age [A], body weight [B], body mass index [C], and heart rate [D].

FIG. 4 indicates the study group characteristics NYHA class [E], UICC cancer disease severity [F] and Karnofsky index [G].

FIG. 5 indicates the study group characteristics for cardiac left ventricular ejection fraction (LVEF triplan [H]), cardiac size (LVEDD [I]), and systolic blood pressure [K] in %.

FIG. 6 indicates the study group characteristics exercise time in seconds [L], objective exercise capacity (peak VO2 per kg body weight in mL/kg/min [M]), and total exercise capacity (i.e. total peak VO2 in mL/min [N]).

FIG. 7 indicates the study group characteristics MR-proANP level [0] and procalcitonin level [P].

FIG. 8 is a Kaplan-Meier survival table for pancreatic cancer patients without significant arrhythmia at 12 months.

FIG. 9 is a Kaplan-Meier survival table for pancreatic cancer patients without significant arrhythmia over time.

FIG. 10A is a Kaplan-Meier survival table for pancreatic cancer patients with significant arrhythmia over time.

FIG. 10B is a Kaplan-Meier survival graph comparing pancreatic cancer patients with and without significant arrhythmia over time.

FIG. 11A is a Cox-proportional Hazard Analysis survival table for pancreatic cancer patients with raised levels of VES (upper panel) and a corresponding baseline cumulative survival plot for Follow-up in days (lower panel).

FIG. 11B is a Cox-proportional Hazard Analysis survival table for pancreatic cancer patients with raised levels of procalcitonin (upper panel) and a corresponding baseline cumulative survival plot for Follow-up in days (lower panel).

FIG. 12 is a regression analysis of MR-proANP level versus exercise capacity in patients.

FIG. 13 is a regression analysis of procalcitonin level versus the frequency of VES in patients over 24 hour ECG at baseline.

DETAILED DESCRIPTION OF THE INVENTION

The invention is based on the surprising finding that the use of cardiac pacemakers, including ICD and CRT devices enhances the performance and general condition of a subject without cardiac illness. Especially the invention enables the reduction of symptoms of shortness of breath, weakness and fatigue, reduces and reverses weight loss, reduces and reverses muscle wasting and reduces death rates in patients with any cancer or with cachexia due to acute or chronic illness other than cardiac illness, including cancer, COPD, chronic renal failure, liver cirrhosis, chronic infections, and AIDS.

In no treatment guideline for cancer, COPD, chronic renal failure, liver cirrhosis, chronic infections, and AIDS the use of pacemakers, particularly of CRT and ICD devices, has been discussed or even suggested to be indicated.

In patients with cardiac illness—particularly for patients with chronic heart failure (CHF) with regards to CRT devices and for patients with coronary artery disease or chronic heart failure and low ejection fraction with regards to ICD devices—the use of such devices leads to better symptom status (CRT devices) or lower mortality (ICD and CRT devices). The implantation of such devices is technically not very difficult and is considered a routine procedure by cardiologists.

The invention is therefore directed to improve the physical performance and general condition of a subject without a cardiac disease, in particular for enabling a therapy for a patient suffering from symptoms of shortness of breath, weakness and fatigue, and/or weight loss.

The inventive method is characterized by the connection of the heart of a patient suffering from cancer or from cachexia due to acute or chronic illness other than cardiac illness with a cardiac pacemaker. Advantageously, the connection can be performed by any standard method or any other known procedure for connecting a heart with a cardiac pacemaker.

Particularly it is preferred, when the heart of a patient suffering from cancer, COPD, chronic renal failure, liver cirrhosis, chronic infections and/or AIDS and/or suffering from other non-cardiac disease causing or associated with cachexia and/or weight loss, is connected with the pacemaker. Most preferably the heart of a patient with cancer, in particular pancreatic cancer, is connected with the cardiac pace maker.

In principle, all possible cardiac pacemakers are appropriate for putting the invention into practice. Preferably a cardiac resynchronisation device (CRT) and/or an automated internal cardiac defibrillator (ICD) is connected with the heart. In a further preferred embodiment of the invention a cardiac resynchronisation device and an automated internal cardiac defibrillator (CRT-D) are connected with the heart.

In another preferred embodiment, the inventive method further comprises the implantation of the cardiac pacemaker in the patient and/or the use of the cardiac pacemaker for regulating the beating of the heart to which it is connected, in particular the use of a cardiac resynchronisation device (CRT) and/or an automated internal cardiac defibrillator (ICD). In a further preferred embodiment of the invention a cardiac resynchronisation device and an automated internal cardiac defibrillator (CRT-D) connected with the heart are used to regulate the beating of the heart.

In a further preferred embodiment, the inventive method, in particular the use of the cardiac pacemaker for regulating the heart beat, is performed in such a way, that the plasma level of natriuretic peptides, in particular ANP and/or BNP, is reduced in the patient.

In particular, it is preferred to execute the inventive method by connecting the cardiac pacemaker with the heart and/or by using the same for regulating the heart beat of a patient with raised levels of natriuretic peptides, particularity with a raised plasma level or raised serum level of ANP, BNP, pro-ANP, NT-proANP NT-proBNP or MR-proANP.

The term "raised levels" as described herein concerns levels/concentrations of natriuretic peptides being significantly higher in the body fluid of a subject without cardiac illness but suffering from cancer or cachexia due to acute or chronic illness other than cardiac illness, including cancer of the prostate, COPD, chronic renal failure, liver cirrhosis, chronic infections, and/or AIDS, in comparison with a healthy subject. In particular the level is considered to be raised when the level is above the upper limit of normal of the respective age- and gender-adjusted normal range as defined from a population of healthy subjects, preferably 1 to 10 times that of the upper limit of normal, more preferable 1 to 4 times that of the upper limit of normal, and even more preferable 1 to 2 times that of the upper limit of normal.

In yet a further preferred embodiment of the inventive method the cardiac pacemaker connected to the heart is used for regulating the heart beat in such a way that intrinsic metabolic changes are induced in the skeletal musculature or in the fat tissue of the patient and/or is used in such a way that the frequency of cardiac arrythmias is reduced and/or that cardiac arrythmias are terminated.

In yet another preferred embodiment of the inventive method the cardiac pacemaker is connected with the heart and/or the cardiac pacemaker is used for regulating the heart beat of a patient with increased frequency of significant arrythmias as assessed in surface ECG or 24 hour ECG, in particular assessed in 3- or 12 channel surface ECG and/or a 24 hour ECG.

In still another preferred embodiment of the invention, the presence of ventricular tachycardia or increased frequency of ventricular extra systolies is diagnosed and/or the presence of raised plasma levels or serum levels of procalcitonin is diagnosed.

Preferably, in the inventive method the cardiac pacemaker is used for regulating the heart beat in such a way that the development of cardiac arrythmias and/or of heart failure is reduced in patients with cancer, who are treated with drugs that are known to be cardiotoxic, and/or if the treatment with the pacemaker is accompanied by the use of a beta-blocker.

It is furthermore preferred to execute the inventive method in its different embodiments if the connection with, the use of, and/or the treatment with the pacemaker is accompanied by the use of an anti-arrhythmic drug, in particular by the use of Amiodarone, Chinidin, Procainamid, Disopyramid, Ajmalin, Lidocain, Mexiletin, Phenytoin, Flecainid, Propafenon, Metoprolol, Bisoprolol, Nebivolov, Dronedaron, Sotalol, Bretylium, Verapimil, Bucindolol, Carvedilol, Atenolol, Propranolol and/or Diltiazem.

In cancer, the invention improves cancer treatment compliance (particularly chemotherapy & radiotherapy), as these are often stopped early because of the poor clinical and symptom status of the patients, and the treatment according to the invention prevents and/or reverses these problems.

Other features and advantages of the invention in its different embodiments will also become apparent from the following detailed description and examples.

1) ICD Devices

It is now concluded that patients with cachexia without cardiac disease have an increased frequency of arrhythmias leading to an increased frequency of sudden death.

To exemplify this, it was found in the work leading to the invention, that in patients with cachexia due to pancreatic cancer in whom it was proven that cardiac disease was not present, the frequency of significant arrythmias in the 24-hour ECG was 66.7% (8 of 12 patients) compared to 16.7% (2 of 12) in healthy controls ($p<0.05$, see example 1).

Examples 2 to 4 provide examples of the inventive kind of treatment and the resulting benefits in patients with any cancer or in patients with cachexia due to acute or chronic illness other than cardiac illness, including cancer, COPD, chronic renal failure, liver cirrhosis, chronic infections, and AIDS.

2) CRT Devices

CRT devices are know to be able to reduce plasma levels of natriuretic peptides in patients with heart disease.

Natriuretic peptides are known to be lipolytic hormones. In the context with the invention it is now concluded therefore that they contribute to fat tissue wasting.

In patients with any cancer or patients with cachexia due to acute or chronic illness other than cardiac illness, including cancer, COPD, chronic renal failure, liver cirrhosis, chronic infections, and AIDS, it is now feasible according to the invention that CRT devices reduce plasma levels of natriuretic peptides, like ANP or BNP.

Hence, according to the invention, CRT devices act to have anti-cachectic effects, which result in clinical benefit (see examples 2 to 4).

In the following practical examples of the invention it is, inter alia, demonstrated that a substantial proportion of patients with cancer suffer from increased frequency of severe arrythmias including ventricular extra systolies (VES) and ventricular tachycardia (VT). (example 5)

that the presence of significant ventricular extra systolies (VES) or of ventricular tachycardia (VT) is associated with increased mortality in patients with cancer who are considered to have no cardiac illness. (example 6)

that a substantial proportion of patients with cancer have raised levels of natriuretic peptides and that these increased levels are associated with poorer exercise capacity. (example 7)

that a substantial proportion of patients with cancer have raised levels of the biomarker procalcitonin and that these increased levels are associated with increased frequency of arrythmias. (example 8)

that a substantial proportion of patients with cancer suffer from prolonged QRS time of the ECG despite normal global cardiac function as measured by echocardiography. (example 9)

Furthermore a practical example for treating different patients suffering of several symptoms is provided (example 10).

EXAMPLE 1

Shortness of Breath in Pancreatic Cancer

The Muscle Hypothesis of Heart Failure Does Apply Beyond Cardiology

Background: In cancer, shortness of breath is frequently seen. Its pathophysiologic origin is unclear. Shortness of breath is a key sign of heart failure, and the muscle hypothesis suggests that this is due to metabolic changes within the skeletal muscle, independently of left ventricular (LV) function. An aim of the work was to test, whether the muscle hypothesis also applies to patients with pancreatic cancer (P-Ca).

Methods: 17 patients with recent onset of P-Ca (age 61±11 yrs, 9 female) were examined, where wasting is known to occur. Symptom limited exercise capacity (treadmill, RQ 1.1±0.1 vs. 1.1±0.1), LV function (echocardiography), 24 hour ECG (consented to by 12 patients) and body composition (DEXA-scan) were assessed. None of the patients had a history of cardiac disease or any clinical sign of cardiac limitation. 12 healthy subjects of similar age served as controls (age 59±7 yrs, 7 female).

Results: LV ejection fraction (LVEF) was not different between controls (63±5%) and P-Ca (61±11%, p=0.55), as was LV end diastolic diameter (LVEDD, 50±6 vs 45±6 mm, p=0.1). BMI (22±3 vs 26±5 kg/m$^2$, p=0.012) was reduced in P-Ca patients. In 8 of 12 P-Ca patients and 2 of 12 controls ectopic ventricular activity was observed in the 24-hour ECG (p<0.05). All P-Ca patients had QRS duration<130 ms. Compared to controls, patients with P-Ca had similar total body lean tissue mass (47±12 vs. 48±9 kg, p=0.65) and bone mineral content (2.5±0.6 vs. 2.6±0.5 kg, p=0.78), but lower total fat tissue mass (12.6±4 vs 22.1±10.4 kg, p=0.002) and fat tissue content (21±7 vs 32±11%, p=0.002). Exercise capacity (exercise time: 12±5 vs 18±6 min, p=0.02, peak VO$_2$ 19±5 vs 26±7 mL/min/kg, p=0.017) and anaerobic threshold (12±2 vs 15±3 mL/min/kg, p=0.02) were reduced in P-Ca patients, but the VE/VCO$_2$-slope was increased (35±9 vs 29±5, p=0.04). In controls, total peak VO$_2$ related to the amount of lean tissue (r=0.9, p<0.0001), but in P-Ca patients this relationship was not present (r=0.5, p=0.1). Consequently, peak VO$_2$ per kg lean tissue was particularly reduced in P-Ca patients (23±9 vs 39±5 mL/min/kg, p<0.0001).

Conclusion: Exercise capacity and ventilatory efficiency are impaired in patients with P-Ca (similar to degrees seen in patients with moderate CHF), but cardiac function and dimensions were normal in these patients. As in cardiac cachexia, the degree of impaired exercise capacity did not relate to lean tissue mass. It is assumed, that symptom generation in P-Ca may be due to intrinsic metabolic changes of the skeletal musculature. Additionally, evidence of severe lipolysis (fat tissue wasting) and ectopic ventricular activity was found in patients with P-Ca. Both could be counter-acted using beta-blocker therapy

EXAMPLE 2

When patients with malignant cancer and cachexia (as evidenced by a body mass index<22 kg/m$^2$ or weight loss>5% compared to the pre-illness normal weight) are treated with a standard ICD device (for instance from the manufacturers Guidant, Medtronic or Biotronic), then the rate of sudden cardiac death is reduced in this cohort and the overall mortality rate decreases. Additionally, this treatment allows more aggressive chemo therapy and radiation therapy.

Also, this treatment—when combined with or replaced by treatment using a CRT device—enables to
a) reduce the frequency and/or intensity of weight loss or reverse prior weight loss, and
b) improve symptom status with regards to shortness of breath and fatigue status, muscle strength and exercise capacity.

EXAMPLE 3

When patients with malignant cancer that requires chemotherapy or radiation therapy are treated with a standard ICD device (for instance from the manufacturers Guidant, Medtronic or Biotronic), then the rate of sudden cardiac death is reduced in this cohort and the overall mortality rate decreases. Additionally, this treatment allows more aggressive chemo therapy and/or radiation therapy.

Also this treatment—when combined with or replaced by treatment using a CRT device—enables to a) reduce the frequency and/or intensity of weight loss or reverse prior weight loss, and b) improve symptom status with regards to shortness of breath and fatigue status, muscle strength and exercise capacity.

EXAMPLE 4

When patients with acute or chronic illness other than cardiac illness, including COPD, chronic renal failure, liver cirrhosis, chronic infections, or AIDS and cachexia (as evidenced by a body mass index<22 kg/m$^2$ or weight loss>5% compared to the pre-illness normal weight) are treated with a standard ICD device (for instance from the manufacturers Guidant, Medtronic or Biotronic), then the rate of sudden cardiac death is reduced in this cohort and the overall mortality rate decreases.

Also this treatment—when combined with or replaced by treatment using a CRT device—enables to a) reduce the frequency and/or intensity of weight loss or reverse prior weight loss, and b) improve symptom status with regards to shortness of breath and fatigue status, muscle strength and exercise capacity.

In the following examples further data is provided to demonstrate the invention as being useful and successful in the areas of application and to prove its practicability and valuable asset. This data is obtained from cancer patients who have no specific cardiac disease, who have no cardiac tumor, and who are not treated with cardiotoxic chemotherapies.

EXAMPLE 5

The research on patients as in example 1 was extended. These patients suffer from pancreatic cancer (P-Ca) with and without cachexia.

Methods: 44 patients with recent onset of P-Ca (mean age 58 yrs, 30% female) were examined, where wasting is known to occur. Symptom limited exercise capacity (treadmill), LV function (echocardiography), 24 hour ECG and survival follow-up as well as neurohormonal assessments were performed.

Assessment of 2 biomarkers: Mid-regional pro-ANP (MR-proANP) was analysed from EDTA plasma, immediately frozen at −80° C. until analysis. Detection of MR-proANP was performed using a sandwich immunoassay (MR-proANP LIA; B.R.A.H.M.S AG, Hennigsdorf/Berlin, Germany) as described in detail in the following reference: Morgenthaler N G, Struck J, Thomas B, Bergmann A. Immunoluminometric assay for the midregion of pro-atrial natriuretic peptide in human plasma. Clin Chem 2004; 50:234-236.

The functional assay sensitivity (inter-assay coefficient of variance<20%) is 20 pmol/L, and the stability of MR-proANP at room temperature is >24 hours This assay allows measurement of MR-proANP in serum and plasma (with EDTA, heparin, or citrate). Median MR-proANP in 325 healthy individuals in previous investigations was 45 pmol/L (95% CI 43-49 pmol/L), reference: Morgenthaler N G, Struck J, Thomas B, Bergmann A. Immunoluminometric assay for the midregion of pro-atrial natriuretic peptide in human plasma. Clin Chem 2004; 50:234-236.

The assessment of procalcitonin as a novel tissue inflammatory marker was performed in plasma using an established test kit (B.R.A.H.M.S AG). For reference see the following publications: a) Morgenthaler N G, Struck J, Fischer-Schulz C, Bergmann A. Sensitive immunoluminometric assay for the detection of procalcitonin. Clin Chem. 2002; 48:788-90. and b) Christ-Crain M, Jaccard-Stolz D, Bingisser R, Gencay M M, Huber P R, Tamm M, Muller B. Effect of procalcitonin-guided treatment on antibiotic use and outcome in lower respiratory tract infections: cluster-randomised, single-blinded intervention trial. Lancet. 2004; 363:600-7.

Results: In the patient group as a whole ventricular arrythmias were more frequent (p<0.01) than in 27 healthy control subjects of similar age. We found a variety of different ventricular and supra-ventricular arrythmias in all but 2 patients. Evidence of severe arrhythmia in 6 patients (14.4%) was found but not in any of the control subjects (p<0.05). The arrythmias consisted of 3 cases of ventricular tachycardia (VT) and 3 cases of >10000 VES in the 24 hour ECG. There were a further 2 cases (4.5%) with 1632 and 5821 VES respectively, which is above the upper boundary of the 95% confidence interval of VES in healthy controls in our population.

In FIGS. 3 to 7 the clinical characteristics of patients with severe arrythmias vs patients without such arrythmias are detailed. The general clinical characteristics (age, BMI, cancer severity as measured by UICC score) Were similar (all p>0.20) as well as markers of cardiac status (LVEF, LVEDD, blood pressure, NYHA class) (all p>0.20). Peak VO2 adjusted for body weight appeared to differ slightly (p=0.084), but total peak VO2 and exercise time were similar (both p>0.3).

Importantly, inserts O and P on FIG. 7 (as well as FIGS. 1 and 2) show that plasma levels of MR-proANP (88 vs 147 pmol/L, p=0.10) and particularly procalcitonin (6.64 vs 0.05 ng/mL, p=0.0009) were increased in patients with severe arrhythmia in P-Ca. These parameters may serve as biomarkers for detecting risk of arrhythmia in cancer.

EXAMPLE 6

In the patients studied in example 5, a follow-up for survival assessment was performed. The follow-up was up to 18 months with a median of 7 months.

Results: Patients with VT or >10000 VES on-24 hour ECG and cancer who do not suffer from known cardiac disease and show no cardiac abnormalities on detailed echocardiographic study do have impaired survival (FIGS. 9, 10A, 10B). The patients with VT or >10000 VES on 24 hour ECG have a 12 month mortality of 68.8% vs a 12 month mortality of 44.1% in patients without such finding.

It was found that raised levels of VES in 24 hour ECG are associated with higher mortality—during up to 18 month follow-up (median 7 months), per 1000 more VES in the 24 hour ECG the mortality risk increased by 5.3% (FIGS. 11A and 11B).

EXAMPLE 7

It was found in further statistical analyses of example 5 that higher MR-proANP levels in cancer patients significantly correlated with worse exercise capacity (FIG. 12). 93% of patients with cancer had abnormal MR-proANP levels (>49 pmol/L), and 15 patients had MR-proANP levels>98 pmol/L.

EXAMPLE 8

It was found in further statistical analyses of example 5 that higher procalcitonin levels in cancer patients highly significantly correlated with higher frequency of VES in the 24 hour ECG (FIG. 13).

EXAMPLE 9

In a subgroup of patients and controls studied in example 5, it was feasible to assess surface ECG's for QRS duration.

Result: In patients with P-Ca, 6 of 25 patients (24%) had an ECG-QRS duration≧120 ms, but none of 12 controls in whom the analysis could be performed (p<0.05).

EXAMPLE 10

If a) a patient with low body mass index (<26 kg/m2) or weight loss (>6% since disease onset) and any cancer, b) a patient with colorectal cancer, non-small cell lung cancer, pancreatic cancer or prostate cancer regardless of the body mass index or weight loss, or c) a patient with any cancer in which a cardio-toxic chemotherapy is performed or planned, is treated according to the invention, then treatment with a) a CRT pacemaker (preferably in patients with ECG-QRS duration>120 ms or a raised natriuretic peptide level) or b) an ICD device (preferably in patients with VT or high number of VES in a 24 hour ECG [e.g. >10000] or with a raised procalcitonin level), or c) with a CRT-D combination device if ≧2 of the ECG and biomarker criteria are fulfilled, then this results in a) prolonged well-being as assessed by better NYHA class or exercise capacity, b) higher hand grip strength, c) better quality of life, d) prevention or delay of development congestive heart failure, e) better survival, f) reduced length and/or frequency of stays in hospital, g) better compliance with chemotherapy regimens, and/or h) better tumor regression as measured by standard statistical criteria.

The characteristics of the invention being disclosed in the preceeding description, the subsequent tables, figures, and claims can be of importance both singularly and in arbitrary combination for the implementation of the invention in its different embodiments.

The foregoing description of preferred embodiments of the invention has been presented for the purposes of illustration and description. It is not intended to be exhaustive or to limit the invention to the precise form described, and many modifications and variations are possible in light of the teaching above.

The embodiments were chosen and described in order to best explain the principles of the invention and its practical applications to thereby enable others skilled in the art to best utilize the invention in various embodiments and with various modifications as are suited to the particular use contemplated. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of treating a patient in need of heart beat regulation, wherein said patient does not suffer from cardiac illness, comprising implanting a cardiac pacemaker into said patient and regulating said patient's heart beat using said implanted cardiac pacemaker.

2. The method of claim 1, wherein said heart beat regulation is effective for at least one of reducing symptoms of shortness of breath, weakness and fatigue, reducing or reversing weight loss, muscle wasting, improving general quality of life, reducing hospitalization length or rate or frequency, reducing cause-specific mortality, and reducing total mortality in said patient.

3. The method of claim 1, wherein said patient is suffering from cancer or from cachexia due to acute or chronic illness other than cardiac illness.

4. The method of claim 1, wherein the patient is suffering from at least one of cancer, COPD, chronic renal failure, liver cirrhosis, chronic infections, AIDS, and other non-cardiac disease causing or associated with cachexia and/or weight loss.

5. The method of claim 2, wherein the patient is suffering from cancer.

6. The method of claim 2, wherein the patient is suffering from pancreatic cancer.

7. The method of claim 1, wherein said regulation improves compliance to cancer therapy.

8. The method of claim 2, wherein the patient is suffering form non-small cell lung cancer.

9. The method of claim 1, wherein the cardiac pacemaker is a cardiac resynchronization device (CRT) and/or an automated internal cardiac defibrillator (ICD).

10. The method of claim 9, wherein the cardiac pacemaker is a cardiac resynchronization device (CRT).

11. The method of claim 9, wherein the cardiac pacemaker is an automated internal cardiac defibrillator (ICD).

12. The method of claim 9, wherein the cardiac pacemaker is a cardiac resynchronization device and an automated internal cardiac defibrillator (CRT-D).

13. The method of claim 1, further comprising the step of reducing said patient's plasma level of natriuretic peptides.

14. The method of claim 13, wherein said natriuretic peptide levels that are reduced are the levels of at least one of ANP and BNP.

15. The method of claim 1, wherein the use of the cardiac pacemaker is conducted in patients with raised levels of natriuretic peptides.

16. The method of claim 15, where the raised level of natriuretic peptides is at least one of a raised plasma level or raised serum level of at least one of ANP, BNP, pro-ANP, NT-proANP, NT-proBNP, or MR-proANP.

17. The method of claim 1, where a raised level of natriuretic peptides is considered to be raised when the level is above an upper limit of normal of the respective age- and gender-adjusted normal range as defined from a population of healthy subjects.

18. The method of claim 1, further comprising inducing intrinsic metabolic changes in said patient's skeletal musculature or fat tissue.

19. The method of claim 1, wherein said patient suffers from cardiac arrythmias in the absence of said regulation and wherein cardiac arrythmias are reduced or terminated by said regulation.

20. The method of claim 1, wherein the use of the cardiac pacemaker is conducted in patients with increased frequency of significant arrythmias as assessed in surface ECG or 24 hour ECG.

21. The method of claim 20, wherein the ECG is a 3- or 12 channel surface ECG or a 24 hour ECG.

22. The method of claim 1, wherein presence of ventricular tachycardia or increased frequency of ventricular extra systolies is diagnosed.

23. The method of claim 1, wherein presence of raised plasma levels or serum levels of procalcitonin is diagnosed.

24. The method of claim 1, wherein the use of the cardiac pacemaker is conducted in such a way that development of cardiac arrythmias and/ of heart failure is reduced in patients with cancer, who are treated with drugs that are known to be cardiotoxic.

25. The method of claim 1, further comprising administering at least one beta-blocker to said patient.

26. The method of claim 25, wherein said at least one beta-blocker is at least one of Metoprolol, Bisoprolol, Bucindolol, Carvedilol, Nebivolol, Sotalol, Atenolol, and Propranolol.

27. The method of claim 1, wherein the treatment with a pacemaker is accompanied by the use of an anti-arrythmic drug.

28. The method of claim 27, wherein anti-arrythmic drug is any one or a combination selected from the group of the drugs Amiodarone, Chinidin, Procainamid, Disopyramid, Ajmalin, Lidocain, Mexiletin, Phenytoin, Flecainid, Propafenon, Metoprolol, Bisoprolol, Bucindolol, Carvedilol, Nebivolol, Atenolol, Propranolol, Dronedaron, Sotalol, Bretylium, Verapamil, Diltiazem.

29. A method of treatment for preventing development of cardiac arrhythmias in a patient in need of such treatment, wherein said patient does not suffer from cardiac arrhythmias, comprising implanting a cardiac pacemaker into said patient and regulating said patient's heart beat using said implanted cardiac pacemaker.

30. A method of reducing a patient's risk of developing a ventricular arrhythmia, wherein said risk is associated with an underlying illness and said patient is suffering from at least one underlying illness selected from cancer, COPD, chronic renal failure, liver cirrhosis, chronic infections, AIDS, and other non- cardiac disease causing or associated with cachexia and/or weight loss, and wherein said patient does not suffer from cardiac illness, comprising implanting a cardiac pacemaker into said patient and regulating said patient's heart beat using said implanted cardiac pacemaker.

* * * * *